US009955088B2

(12) United States Patent
Motzer et al.

(10) Patent No.: US 9,955,088 B2
(45) Date of Patent: Apr. 24, 2018

(54) HYPERSPECTRAL BORESCOPE SYSTEM (71) Applicant: The Boeing Company, Chicago, IL (US)

(72) Inventors: William P. Motzer, Charleston, SC (US); Gary Ernest Georgeson, Tacoma, WA (US); Morteza Safai, Newcastle, WA (US)

(73) Assignee: THE BOEING COMPANY, Chicago, IL (US)

( * ) Notice: Subject to any disclaimer, the term of this patent is extended or adjusted under 35 U.S.C. 154(b) by 154 days.

(21) Appl. No.: 15/178,617

(22) Filed: Jun. 10, 2016

(65) Prior Publication Data

US 2017/0359529 A1 Dec. 14, 2017

(51) Int. Cl.
G01J 3/28 (2006.01)
H04N 5/33 (2006.01)
H04N 5/225 (2006.01)
G06T 7/00 (2017.01)

(52) U.S. Cl.
CPC ........... *H04N 5/332* (2013.01); *G06T 7/0004* (2013.01); *H04N 5/2252* (2013.01); *H04N 5/2256* (2013.01); *G06T 2207/30156* (2013.01); *H04N 2005/2255* (2013.01)

(58) Field of Classification Search
CPC .... H04N 5/332; H04N 5/2252; H04N 5/2256; H04N 7/18; G02B 23/24; G01J 3/02; G01J 3/28; G01J 3/10; G06T 7/0004; B25J 19/023
See application file for complete search history.

(56) References Cited

U.S. PATENT DOCUMENTS 8,836,934 B1 9/2014 Safai et al.
9,046,419 B2 * 6/2015 Yelin .......................... G01J 3/10
2014/0031624 A1 1/2014 Godo et al.

FOREIGN PATENT DOCUMENTS

WO WO2011149576 A1 12/2011
WO WO2013172887 A1 11/2013

OTHER PUBLICATIONS

Extended European Search Report, dated Sep. 21, 2017, regarding Application No. EP17159032.6, 8 pages.

* cited by examiner

*Primary Examiner* — Abdullahi Nur
(74) *Attorney, Agent, or Firm* — Yee & Associates, P.C.

(57) ABSTRACT

A method and apparatus for inspecting a structure. Electromagnetic radiation is sent to a surface on a structure from an electromagnetic radiation emission system. A response is filtered to the electromagnetic radiation using a filter located inside of a borescope inspection housing. The filter is configured to pass a number of wavelengths in a response to the electromagnetic radiation directed at the surface on the structure. Data is generated from the number of wavelengths from the number of wavelengths passed through the filter using a sensor array. A two-dimensional image of the surface on the structure is generated with a group of graphical indicators indicating a group of inconsistencies not visible to a naked eye. The two-dimensional image is generated using data from a sensor array.

21 Claims, 7 Drawing Sheets

HYPERSPECTRAL BORESCOPE SYSTEM

BACKGROUND INFORMATION

1. Field

The present disclosure relates generally to aircraft and, in particular, to aircraft inspection systems. Still more particularly, the present disclosure is related to a method and apparatus for inspecting an aircraft using a borescope system.

2. Background

Aircraft are being designed and manufactured with greater and greater percentages of composite materials. Composite materials are used in aircraft to decrease weight of the aircraft. This decreased weight improves performance features such as payload capacities and fuel efficiencies. Further, composite materials provide longer service life for various components in the aircraft.

Composite materials are tough, light-weight materials created by combining two or more functional components. For example, a composite material may include reinforcing fibers bound in a polymer resin matrix. The fibers may be unidirectional or may take the form of a woven cloth or fabric. The fibers and resins are arranged and cured to form a composite material.

Further, using composite materials to create aerospace composite structures potentially allows for portions of an aircraft to be manufactured in larger pieces or sections. For example, a fuselage in an aircraft may be created in cylindrical sections to form the fuselage of the aircraft. Other examples include, without limitation, wing sections joined to form a wing or stabilizer sections joined to form a stabilizer.

In manufacturing composite structures, layers of composite material are typically laid up on a tool. The layers may be comprised of fibers in sheets. These sheets may take the form of fabrics, tape, tows, or other suitable forms. In some cases, resin may be infused or preimpregnated into the sheets. These types of sheets are commonly referred to as prepreg.

The different layers of prepreg may be laid up in different orientations, and different numbers of layers may be used depending on the thickness of the composite structure being manufactured. After the different layers have been laid up, the layers are consolidated and cured upon exposure to temperature and pressure, thus forming the final composite structure.

Inspections of the composite structure may be made at different times such as during the layout of the layers of prepreg, after the composite structure has been formed prior to curing the composite structure, and after curing the composite structure. The inspection may be performed using x-ray inspection systems, ultrasound inspection systems, and other types of non-destructive inspection systems.

Visual inspections also may be made with an operator visually inspecting the composite structure in addition to other types of inspection systems. The visual inspection may be made to locate inconsistencies such as foreign object debris (FOD), delamination, or other inconsistencies. These types of inspections may be more difficult to make than desired in some composite structures because of limited access to an interior or other locations. For example, with a composite wing, spars, ribs, and skin panels may be formed individually and placed to form the composite wing prior to co-curing the composite wing. Visually inspecting the interior of the composite wing prior to curing and after curing may be more challenging than desired.

Therefore, it would be desirable to have a method and apparatus that take into account at least one of the issues discussed above, as well as possibly other issues. For example, it would be desirable to have a method and apparatus that overcome a technical problem with inspecting a composite structure with limited access locations.

SUMMARY

An embodiment of the present disclosure provides an apparatus comprising a borescope inspection housing, an electromagnetic radiation emission system associated with the borescope inspection housing, a filter, and a sensor array. The electromagnetic radiation emission system is configured to emit electromagnetic radiation. The filter is located inside of the borescope inspection housing. The filter is configured to pass a number of wavelengths in a response to the electromagnetic radiation directed at a surface on a structure. The response is received through an opening in the borescope inspection housing. The sensor array is located behind the filter inside of the borescope inspection housing. The sensor array comprises sensors configured to generate data from the number of wavelengths passed by the filter, enabling a hyperspectral analysis of the surface on the structure.

Another embodiment of the present disclosure provides a hyperspectral borescope system. The hyperspectral borescope system comprises a borescope inspection housing for a borescope, a tube associated with the borescope inspection housing for the borescope, an electromagnetic radiation emission system associated with the borescope inspection housing, a filter located inside of the borescope inspection housing, a sensor array located behind the filter inside of the borescope inspection housing, and an analyzer in communication with the sensor array. The electromagnetic radiation emission system is configured to emit electromagnetic radiation. The filter is configured to pass a number of wavelengths in a response to the electromagnetic radiation directed at a surface on a structure. The response is received through an opening in the borescope inspection housing. The sensor array comprises sensors configured to generate data from the number of wavelengths passed by the filter. The analyzer is configured to cause the sensor array to generate the data from the response received from the electromagnetic radiation directed to the surface on the structure and generate a two-dimensional image of the surface on the structure with a group of graphical indicators indicating a group of inconsistencies not visible to a naked eye.

Yet another embodiment of the present disclosure provides a method for inspecting a structure. Electromagnetic radiation is sent to a surface on a structure from an electromagnetic radiation emission system. A response is filtered to the electromagnetic radiation using a filter located inside of a borescope inspection housing. The filter is configured to pass a number of wavelengths in a response to the electromagnetic radiation directed at the surface on the structure. Data is generated from the number of wavelengths from the number of wavelengths passed through the filter using a sensor array. A two-dimensional image of the surface on the structure is generated with a group of graphical indicators indicating a group of inconsistencies not visible to a naked eye. The two-dimensional image is generated using data from a sensor array.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

The illustrative embodiments recognize and take into account one or more different considerations. For example, the illustrative embodiments recognize and take into account that a visual inspection may be more difficult to make than desired when a composite structure has locations with limited access. The illustrative embodiments also recognize and take into account that a borescope may be used to perform the visual inspection.

For example, the illustrative embodiments recognize and take into account that an operator may use the borescope to look for inconsistencies on a surface on a composite structure. The illustrative embodiments recognize and take into account, however, that currently used borescopes only provide a limited ability to inspect the surface on a composite structure. The illustrative embodiments also recognize and take into account that currently used borescopes only allow an operator to view the inconsistencies that can be seen with a naked eye.

Thus, the illustrative embodiments provide a method and apparatus for inspecting a structure for an aircraft, including composite structures, for the inconsistencies. In one illustrative example, an apparatus comprises a borescope inspection housing, an electromagnetic radiation emission system, a filter, and a sensor array. The electromagnetic radiation emission system is associated with the inspection housing in which the electromagnetic radiation source is configured to emit electromagnetic radiation. The filter is located inside of the inspection housing and is configured to pass a number of wavelengths in a response to the electromagnetic radiation directed at a surface on a structure. The response is received through an opening in the inspection housing. The sensor array is located behind the filter inside of the inspection housing, wherein the sensor array comprises sensors configured to generate data from the number of wavelengths passed by the filter, thus enabling a hyperspectral analysis of the surface on the structure.

When one component is "associated" with another component, the association is a physical association. For example, a first component, such as an electromagnetic radiation emission system, may be considered to be physically associated with a second component, such as a borescope inspection housing, by at least one of being secured to the second component, bonded to the second component, mounted to the second component, welded to the second component, fastened to the second component, or connected to the second component in some other suitable manner. The first component also may be connected to the second component using a third component. The first component may also be considered to be physically associated with the second component by being formed as part of the second component, an extension of the second component, or both.

Figure 1:
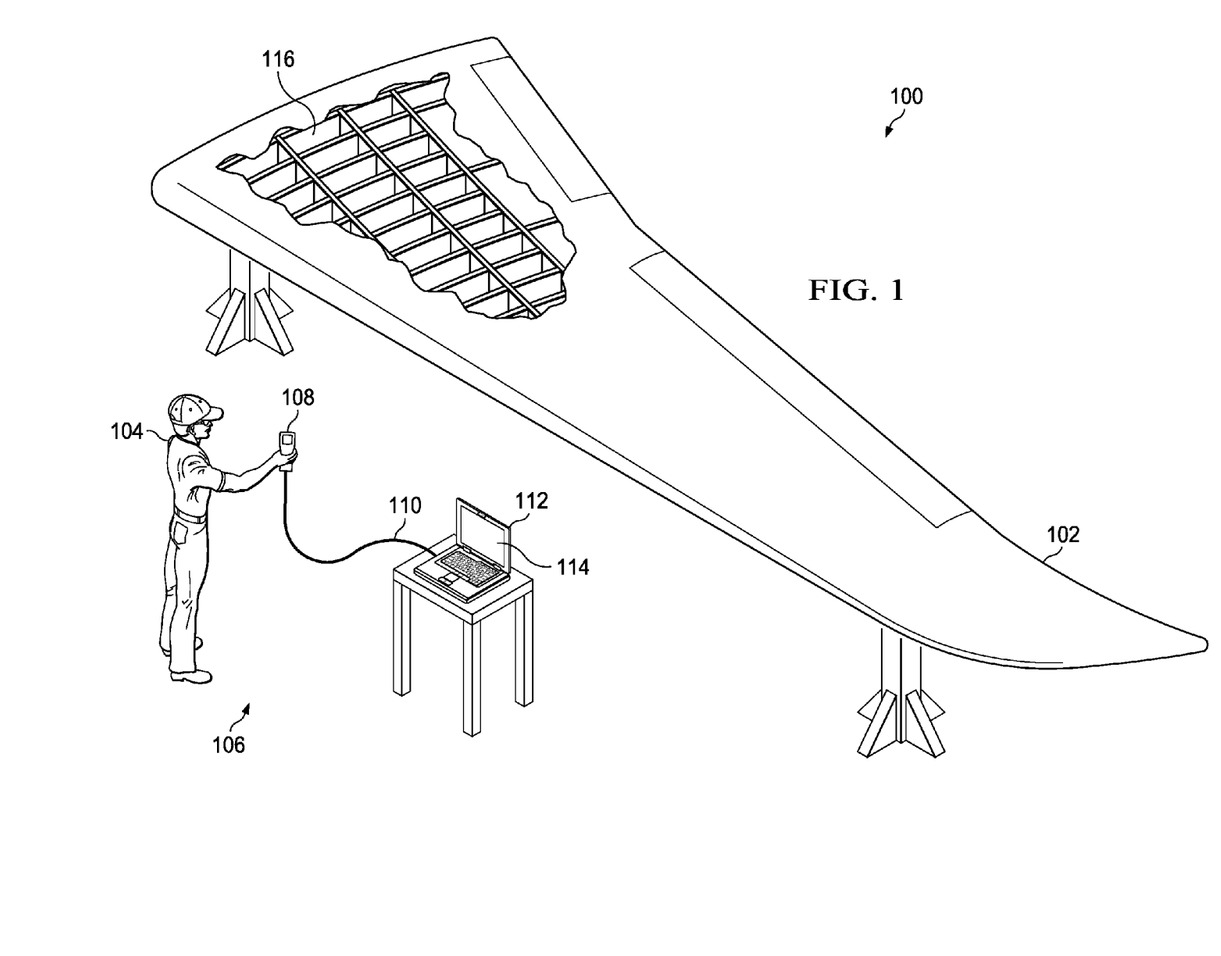
FIG. 1 is an illustration of an aircraft inspection environment in accordance with an illustrative embodiment.

With reference now to the figures and, in particular, with reference to FIG. 1, an illustration of an aircraft inspection environment is depicted in accordance with an illustrative embodiment. In this depicted example, aircraft inspection environment 100 includes composite wing 102. Composite wing 102 is in an uncured form and shown in an exposed view. The different parts forming composite wing 102 may be co-cured to place composite wing 102 in cured form for use on an aircraft.

In this illustrative example, operator 104 is a human operator that performs an inspection of composite wing 102. Operator 104 uses borescope system 106 to inspect composite wing 102. As depicted, borescope system 106 includes borescope inspection head 108, cable 110, computer 112, and display device 114.

As depicted, operator 104 may move borescope inspection head 108 into interior 116 of composite wing 102 using cable 110. Cable 110 provides a connection between borescope inspection head 108 and computer 112 in addition to being used to position borescope inspection head 108 within interior 116 of composite wing 102 as seen in this exposed view of composite wing 102.

In this illustrative example, borescope inspection head 108 generates information about surfaces within interior 116 of composite wing 102 and sends the information to computer 112. This information may be used to perform hyperspectral analysis of surfaces within interior 116. Images may be generated and displayed on display device 114 for use in visualizing the hyperspectral analysis.

In this manner, inconsistencies not visible to the naked eye may be identified using borescope system 106. Additionally, borescope system 106 also may be used to display images of surfaces within interior 116 of composite wing 102 without hyperspectral analysis.

The illustration of aircraft inspection environment 100 in FIG. 1 is provided as one example of an illustrative embodiment and not meant to limit the manner in which other illustrative embodiments may be implemented. For example, borescope system 106 may be used to inspect surfaces that are more easily accessible in addition to surfaces that have limited access. As another example, borescope system 106 may be used to inspect other structures other than composite wing 102. For example, borescope system 106 may be used to inspect a skin panel, a fuselage, a wing box, a spar, or some other suitable structure that may be comprised of at least one of a composite material, a metal, a plastic, or some other suitable material.

As used herein, the phrase "at least one of", when used with a list of items, means different combinations of one or more of the listed items may be used, and only one of each item in the list may be needed. In other words, "at least one of" means any combination of items and number of items may be used from the list, but not all of the items in the list are required. The item may be a particular object, a thing, or a category.

For example, without limitation, "at least one of item A, item B, or item C" may include item A, item A and item B, or item B. This example also may include item A, item B, and item C or item B and item C. Of course, any combinations of these items may be present. In some illustrative examples, "at least one of" may be, for example, without limitation, two of item A; one of item B; and ten of item C; four of item B and seven of item C; or other suitable combinations.

Figure 2:
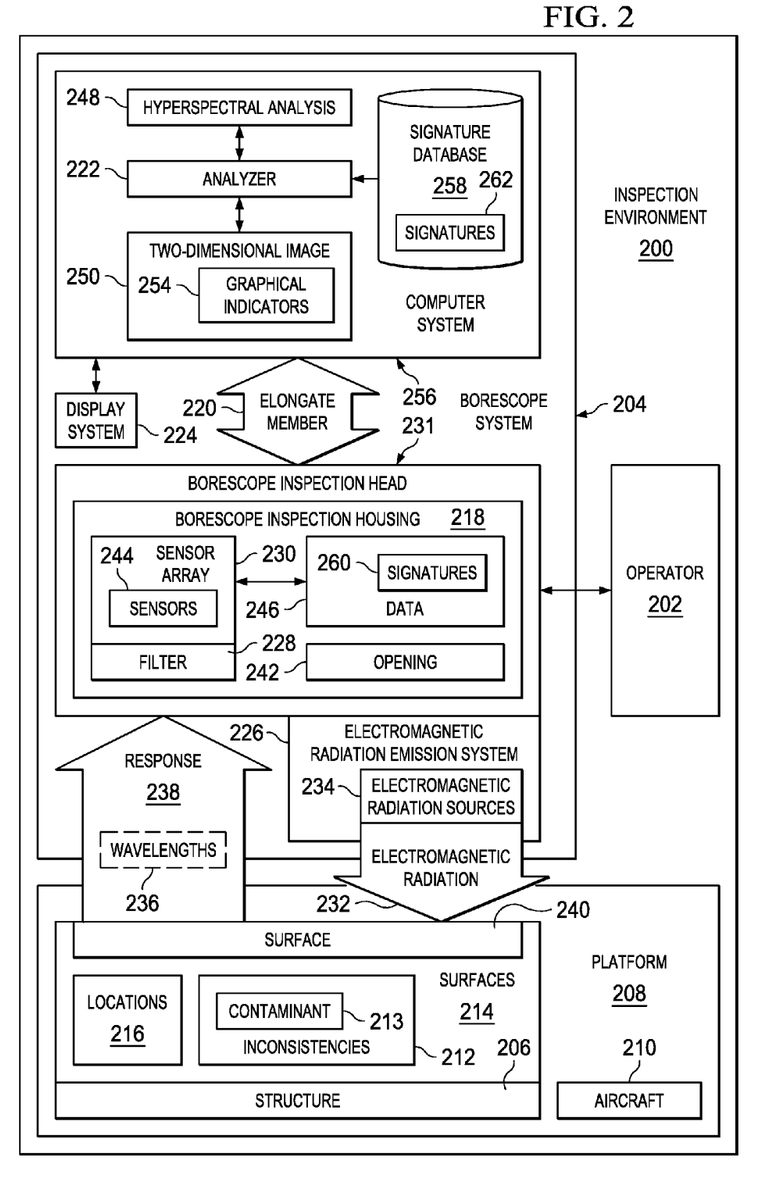
FIG. 2 is an illustration of a block diagram of an inspection environment in accordance with an illustrative embodiment.

With reference next to FIG. 2, an illustration of a block diagram of an inspection environment is depicted in accordance with an illustrative embodiment. Aircraft inspection environment 100 in FIG. 1 is an example of one implementation of inspection environment 200 shown in block form in this figure.

As depicted, operator 202 is a human operator that uses borescope system 204 to inspect structure 206 for platform 208. In this illustrative example, platform 208 takes the form of aircraft 210.

In this illustrative example, operator 202 may use borescope system 204 to determine whether a group of inconsistencies 212 is present on a group of surfaces 214 on structure 206. Structure 206 may take a number of different forms. For example, structure 206 may be selected from one of an uncured composite structure, a cured composite structure, a part, an assembly, a wing, a composite skin panel, a horizontal stabilizer, a spar, a rib, layers of prepreg, an engine housing, a wing box, a pipe, a tube, or some other suitable type of structure. The group of surfaces 214 on structure 206 may include a group of locations 216 that is difficult to access without borescope system 204.

In this illustrative example, the group of inconsistencies 212 may take a number of different forms. For example, the group of inconsistencies 212 may be selected from at least one of foreign object debris (FOD), a delamination, a smudge, or some other undesired condition. The undesired condition may be a condition that does not meet specifications for structure 206.

Further, the group of inconsistencies 212 may not be detrimental to the structure being inspected. Instead, the group of inconsistencies 212 may indicate the presence of an issue or problem. For example, the group of inconsistencies 212 may be a presence of fuel residue at a location on a surface in the first structure in which the fuel residue should not normally be found. This fuel residue is an inconsistency in the group of inconsistencies 212 that may indicate the presence of a leak in a second structure.

In the illustrative example, the group of inconsistencies 212 may include contaminant 213. Contaminant 213 is any physical, chemical, biological, or radiological substance that causes structure 206 to not perform as desired. The reduction in performance may be, for example, reduced strength, corrosion resistance, smoothness, aesthetics, or some other type of performance.

In this illustrative example, borescope system 204 has a number of different components. As depicted, borescope system 204 comprises borescope inspection housing 218, elongate member 220, analyzer 222, and display system 224.

Elongate member 220 connects borescope inspection housing 218 and analyzer 222 to each other. Depending on the particular implementation, elongate member 220 may be flexible or rigid. For example, elongate member 220 may be selected from one of a rigid elongate member, a flexible elongate member, a cable, a tube, a pipe, or some other suitable type of elongate member. Elongate member 220 may be used by operator 202 to move borescope inspection housing 218 to the group of locations 216 on the group of surfaces 214.

In this illustrative example, borescope inspection housing 218 serves as a platform for a number of different components. As depicted, these components include electromagnetic radiation emission system 226, filter 228, and sensor array 230. These components and borescope inspection housing 218 form borescope inspection head 231.

Borescope inspection housing 218 may be comprised of any number of materials. For example, borescope inspection housing 218 may be comprised of one or more materials selected from aluminum, steel, plastic, a composite material, titanium, polycarbonate, or some other suitable material. The material selected is based on the environment in which borescope inspection housing 218 is used or other factors.

Electromagnetic radiation emission system 226 is associated with borescope inspection housing 218. As depicted, electromagnetic radiation emission system 226 is configured to emit electromagnetic radiation 232. In this illustrative example, electromagnetic radiation emission system 226 comprises a group of electromagnetic radiation sources 234 that emit electromagnetic radiation 232.

As depicted, filter 228 is located inside of borescope inspection housing 218. Filter 228 is configured to pass a number of wavelengths 236 in response 238 to electromagnetic radiation emission system 226 directed at surface 240 in surfaces 214 on structure 206. Filter 228 is an interference filter in this illustrative example. Response 238 is received through opening 242 in borescope inspection housing 218.

In the illustrative example, sensor array 230 is located behind filter 228 inside of borescope inspection housing 218. Sensor array 230 comprises sensors 244 that are configured to generate data 246 from the number of wavelengths 236 that are passed by filter 228. Sensors 244 may take a number of different forms. For example, sensors 244 may be selected from at least one of a charged coupled device, a complementary metal oxide semiconductor device, an indium antimonide (InSb) semiconductor device, a mercury cadmium telluride (HgCdTe) semiconductor device, or some other suitable type of device that detects electromagnetic radiation.

As used herein, "a number of," when used with reference to items, means one or more items. For example, "a number of wavelengths 236" is one or more of wavelengths 236.

The generation of data 246 enables hyperspectral analysis 248 of surface 240 on structure 206 by analyzer 222. In the illustrative example, hyperspectral analysis 248 involves analyzing information in a spectrum of wavelengths 236.

Wavelengths 236 in response 238 are filtered to obtain the group of wavelengths 236 that may be of interest for analysis. The spectrum of wavelengths 236 may include at least one of visible, near infrared, ultraviolet, microwave, or other suitable wavelengths.

For example, analyzer 222 is in communication with sensor array 230 such that analyzer 222 is able to control the operation of sensor array 230 and receives data 246 generated by sensor array 230. Analyzer 222 communicates with sensor array 230 using at least one of an electrical wire, an optical fiber, or a wireless connection. When the communication is implemented with a physical communications link, such as electrical wire or optical fiber, the communications link may extend through elongate member 220.

As depicted, analyzer 222 is configured to cause sensor array 230 to generate data 246 from response 238 received from electromagnetic radiation 232 directed to surface 240 on structure 206. Analyzer 222 is also configured to generate two-dimensional image 250 of surface 240 on structure 206 with a group of graphical indicators 254 indicating a group of inconsistencies 212 not visible to the naked eye. In this example, two-dimensional image 252 may include structure 206. The placement of the group of graphical indicators 254 in two-dimensional image 250 may be at locations 216 on structure 206 where the group of inconsistencies 212 has been identified. Further, the group of graphical indicators 254 also may include an indication of when an inconsistency is absent.

The group of graphical indicators 254 may take a number of different forms. For example, the group of graphical indicators 254 may be selected from at least one of a color, bolding, text, an icon, a flashing graphic, or some other suitable graphical indicator to indicate the presence or absence of the inconsistency.

Analyzer 222 may be implemented in software, hardware, firmware, or a combination thereof. When software is used, the operations performed by analyzer 222 may be implemented in program code configured to run on hardware, such as a processor unit. When firmware is used, the operations performed by analyzer 222 may be implemented in program code and data and stored in persistent memory to run on a processor unit. When hardware is employed, the hardware may include circuits that operate to perform the operations in analyzer 222.

In the illustrative examples, the hardware may take a form selected from at least one of a circuit system, an integrated circuit, an application specific integrated circuit (ASIC), a programmable logic device, or some other suitable type of hardware configured to perform a number of operations. With a programmable logic device, the device may be configured to perform the number of operations. The device may be reconfigured at a later time or may be permanently configured to perform the number of operations. Programmable logic devices include, for example, a programmable logic array, a programmable array logic, a field programmable logic array, a field programmable gate array, and other suitable hardware devices. Additionally, the processes may be implemented in organic components integrated with inorganic components and may be comprised entirely of organic components, excluding a human being. For example, the processes may be implemented as circuits in organic semiconductors.

In this example, analyzer 222 may be implemented in computer system 256, which is a physical hardware system and includes one or more data processing systems. When more than one data processing system is present, those data processing systems are in communication with each other using a communications medium. The communications medium may be a network. The data processing systems may be selected from at least one of a computer, a server computer, a tablet, or some other suitable data processing system.

As depicted, analyzer 222 may perform hyperspectral analysis 248 to identify inconsistencies 212 using data 246 and signature database 258. As depicted, data 246 includes a group of signatures 260 based on response 238 detected by sensor array 230. For example, data 246 includes data generated from the group of wavelengths 236 separated out from response 238 for each of the group of locations 216. In these illustrative examples, data 246 includes an intensity for each wavelength in the group of wavelengths 236 for a particular location in the group of locations 216. The portion of data 246 for a particular location in the group of locations 216 forms a signature in these examples.

The group of signatures 260 in data 246 is compared to a group of signatures 262 in signature database 258 to determine whether inconsistencies 212 are present. Signature database 258 is a database of wavelengths for known inconsistencies. Each of signatures 262 is for a particular inconsistency. Each of signatures 262 contains the wavelengths and intensities for those wavelengths that are present when the particular inconsistency is present. The wavelengths and intensities are selected to be unique for a material in the illustrative examples.

Further, signatures 262 also may include signatures for conditions when an inconsistency is not present. For example, signatures 262 may include signatures for a composite material, a metal, or other suitable materials that may be present when inconsistencies 212 are absent. Thus, analyzer 222 may identify the material present for a structure in response 238 in addition to whether an inconsistency is present.

Thus, borescope system 204 is a hyperspectral borescope system. In this manner, inspections may be performed to identify inconsistencies 212 that are not visible to the naked eye. In one illustrative example, one or more technical solutions are present that overcome a technical problem with inspecting a composite structure with limited access locations. One or more technical solutions employ borescope system 204 that allow for hyperspectral analysis 248.

As a result, one or more technical solutions may provide a technical effect of enabling an ability to identify a group of inconsistencies 212 on surface 240 on structure 206, even where surface 240 on structure 206 has limited access. Also, a technical effect is present in which the group of inconsistencies 212 also may be identified even when not apparent to the naked eye of operator 202.

Figure 3:
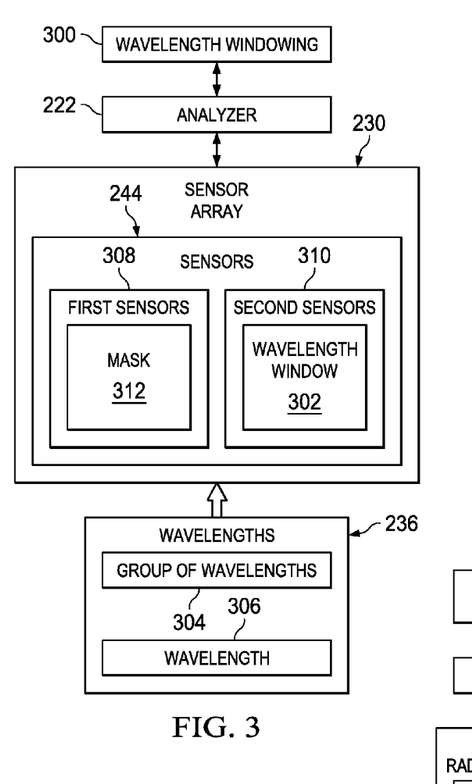
FIG. 3 is an illustration of a block diagram of wavelength windowing in a borescope system in accordance with an illustrative embodiment.

With reference next to FIG. 3, an illustration of a block diagram of wavelength windowing in a borescope system is depicted in accordance with an illustrative embodiment. In this example, analyzer 222 controls the operation of sensors 244 in sensor array 230 to perform wavelength windowing 300 in borescope system 204 in FIG. 2.

As depicted, analyzer 222 is in communication with sensor array 230. In this illustrative example, analyzer 222 is configured to selectively activate a group of sensors 244 in sensor array 230 to form wavelength window 302 that receives group of wavelengths 304 in a number of wavelengths 236. The number of wavelengths 236 is detected by sensors 244 and some of the number of wavelengths 236 may reach more of sensors 244 than other wavelengths in the number of wavelengths 236.

For example, wavelength 306, known to be part of a normal response, may reach so many of sensors 244 that the detection of this wavelength results in saturation of sensors 244. Wavelength window 302 may be selected to turn off first sensors 308 in sensors 244 that detected wavelength 306. As a result, first sensors 308 do not generate signals or data for wavelength 306.

Second sensors 310 are turned on to detect group of wavelengths 304 that reach second sensors 310. In this example, second sensors 310 form wavelength window 302. First sensors 308 may be considered mask 312. In this manner, saturation by wavelength 306 may be reduced or avoided.

Wavelength window 302 may take different shapes and may include non-contiguous areas of sensors 244. For example, wavelength window 302 may be selected to include sensors 244 in a row, a column, a square, or some other shape. In this illustrative example, group of wavelengths 304 is selected based on the wavelengths for inconsistencies, such as potential contaminants not visible to the naked eye on surface 240 on structure 206 in FIG. 2.

Figure 4:
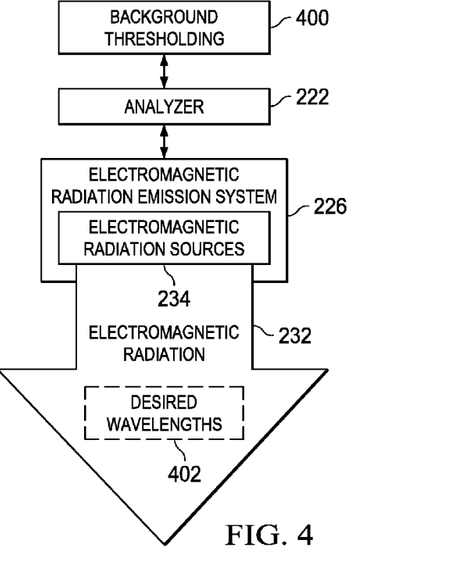
FIG. 4 is an illustration of a block diagram of background thresholding in a borescope system in accordance with an illustrative embodiment.

Turning next to FIG. 4, an illustration of a block diagram of background thresholding in a borescope system is depicted in accordance with an illustrative embodiment. In this example, analyzer 222 controls the operation of electromagnetic radiation sources 234 in electromagnetic radiation emission system 226 to perform background thresholding 400 in borescope system 204 in FIG. 2. Electromagnetic radiation sources 234 may be selected from at least one of a light emitting diode, a halogen light bulb, an incandescent light bulb, or some other suitable type of electromagnetic radiation source.

Wavelengths 236 are present in response 238 prior to being filtered by filter 228 to pass the number of wavelengths 236 in FIG. 2. The composition of wavelengths 236 may be controlled based on a group of desired wavelengths 402 in electromagnetic radiation 232 in FIG. 2.

In the illustrative example, analyzer 222 is in communication with electromagnetic radiation emission system 226. Analyzer 222 is configured to control the operation of electromagnetic radiation emission system 226 and, in particular, electromagnetic radiation sources 234 in electromagnetic radiation emission system 226. As depicted, analyzer 222 selectively activates electromagnetic radiation sources 234 in electromagnetic radiation emission system 226 to cause electromagnetic radiation emission system 226 to emit electromagnetic radiation 232 with the group of desired wavelengths 402.

The selection of wavelengths in the group of desired wavelengths 402 may be based on wavelengths that a particular inconsistency will scatter or reflect for detection in response 238 in FIG. 2. For example, the group of desired wavelengths 402 may be selected based on wavelengths for potential contaminants not visible to the naked eye on surface 240 on structure 206 in FIG. 2. Further, analyzer 222 may select the group of desired wavelengths 402 to inspect surface 240 on structure 206 for a particular type of inconsistency in the group of inconsistencies 212 in FIG. 2. For example, the group of desired wavelengths 402 may be selected for detecting moisture, oil, or some other substance that is considered to be a contaminant when present on surface 240 on structure 206.

The illustrations of inspection environment 200 and the different components in inspection environment 200 in FIGS. 2-5 are not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, although the illustrative examples are described with respect to platform 208 in the form of aircraft 210 in FIG. 2, an illustrative example may be applied to other types of platforms. Platform 208 may be, for example, a mobile platform, a stationary platform, a land-based structure, an aquatic-based structure, and a space-based structure. More specifically, platform 208 may be a surface ship, a tank, a personnel carrier, a train, a spacecraft, a space station, a satellite, a submarine, an automobile, a power plant, a bridge, a dam, a house, a manufacturing facility, a building, and other suitable platforms.

Figure 5:
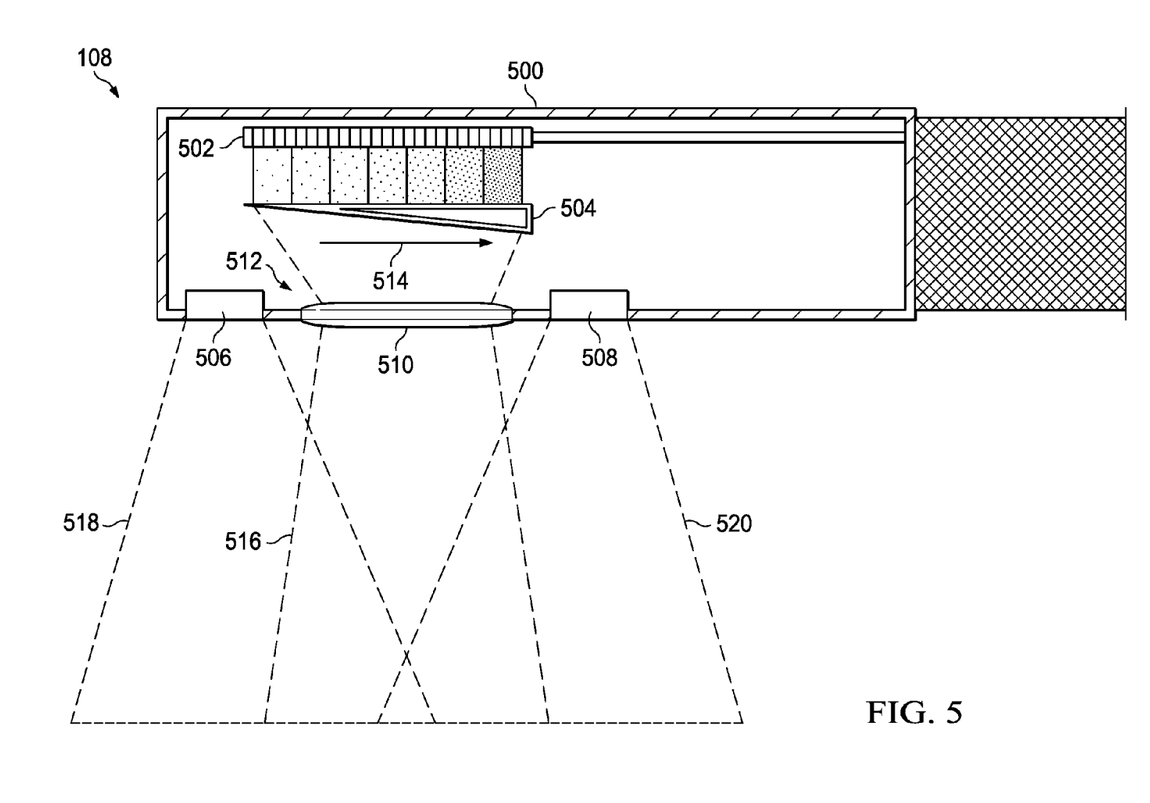
FIG. 5 is an illustration of a borescope head for a borescope inspection system in accordance with an illustrative embodiment.

Turning next to FIG. 5, an illustration of a borescope head for a borescope inspection system is depicted in accordance with an illustrative embodiment. In this illustrative example, a cross-sectional view of borescope inspection head 108 is shown. As depicted, borescope inspection head 108, which includes borescope inspection housing 500, is a platform for complementary metal oxide semiconductor (CMOS) sensor array 502, interference filter 504, illumination diode 506, illumination diode 508, and lens 510.

Borescope inspection housing 500 is an example of an implementation for borescope inspection housing 218 shown in block form in FIG. 2. As depicted, borescope inspection housing 500 is formed out of aluminum.

CMOS sensor array 502 and interference filter 504 are both located inside of borescope inspection housing 500. CMOS sensor array 502 is located behind interference filter 504. Illumination diode 506 and illumination diode 508 are associated with borescope inspection housing 500.

Lens 510 is located in opening 512 in borescope inspection housing 500. As depicted, lens 510 seals opening 512 in borescope inspection housing 500, wherein a response passes through lens 510 to reach interference filter 504.

In this illustrative example, lens 510 may take various forms. For example, lens 510 may allow the response to pass without changing the response. In other illustrative examples, lens 510 may be selected from one of a binary lens, a Fresnel lens, a polarizing lens, or some other suitable type of lens.

When a seal is present, the seal may be a hermetic seal for borescope inspection housing 500. Additionally, borescope inspection housing 500 may be filled with a fluid, such as nitrogen, helium, or some other inert gas, in a manner that provides a positive pressure within borescope inspection housing 500. In another illustrative example, a vacuum may be applied to borescope inspection housing 500 to create a negative pressure.

As depicted, CMOS sensor array 502 is an example of an implementation for sensor array 230 shown in block form in FIG. 2. Interference filter 504, located in front of CMOS sensor array 502, is an example of filter 228 shown in block form in FIG. 2. In this illustrative example, interference filter 504 has a wedge shape and is multilayered such that different wave lengths are passed over different sections of interference filter 504 in the direction of arrow 514 when response 516 is received through lens 510 in opening 512 in borescope inspection housing 500.

Illumination diode 506 and illumination diode 508 are associated with borescope inspection housing 500 to emit electromagnetic radiation in the form of light. For example, illumination diode 506 emits light 518 and illumination diode 508 emits light 520. The light from these illumination diodes may have a range of frequencies.

For example, illumination diode 506 and illumination diode 508 may each emit light in different wavelengths. For example, illumination diode 506 may emit visible light while illumination diode 508 may emit near infrared (IR) light.

For example, other illumination diodes may be present that emit light in the same wavelengths as illumination diode 506 and illumination diode 508 or in other wavelengths, such as ultraviolet light, mid infrared light, far infrared light, or light with other wavelengths.

Figure 6:
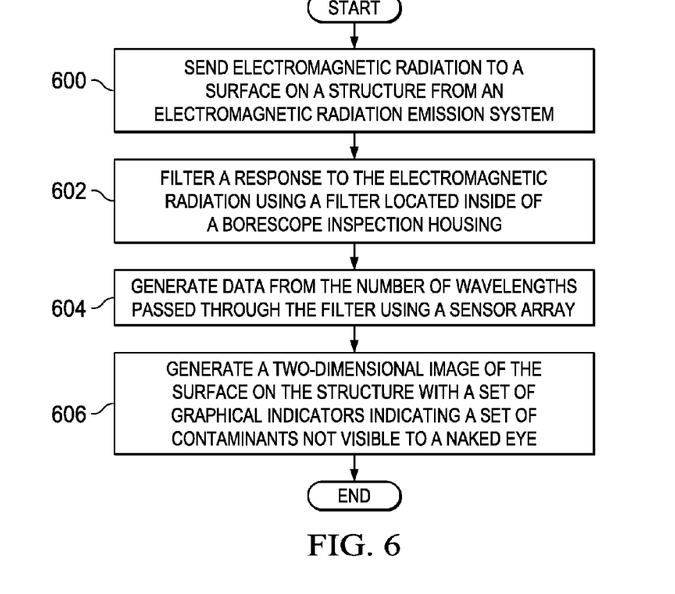
FIG. 6 is an illustration of a flowchart of a process for inspecting a structure in accordance with an illustrative embodiment.

Turning next to FIG. 6, an illustration of a flowchart of a process for inspecting a structure is depicted in accordance with an illustrative embodiment. The process illustrated in FIG. 6 may be implemented using borescope system 204 in FIG. 2. One or more of these operations may be implemented in analyzer 222 in FIG. 2.

The process begins by sending electromagnetic radiation to a surface on a structure from an electromagnetic radiation emission system (operation 600). The process filters a response to the electromagnetic radiation using a filter located inside of a borescope inspection housing (operation 602). The filter is configured to pass a number of wavelengths in response to the electromagnetic radiation directed at the surface on the structure.

The process generates data from the number of wavelengths passed through the filter using a sensor array (operation 604). The process generates a two-dimensional image of the surface on the structure with a group of graphical indicators indicating a set of contaminants not visible to a naked eye (operation 606) with the process terminating thereafter. The two-dimensional image is generated using the data from the sensor array.

With the inspection performed in the process in FIG. 6, rework or replacement of a structure may be performed. With the use of borescope system 204 in FIG. 2 in the process in FIG. 6, the inspection allows for an identification of inconsistencies that are not visible to the naked eye and an ability to make the inspection in locations on the surface that are not easily accessible.

Figure 7:
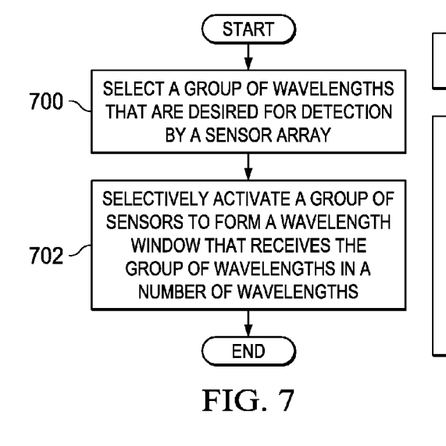
FIG. 7 is an illustration of a flowchart of a process for controlling sensors in a sensor array in accordance with an illustrative embodiment.

Turning to FIG. 7, an illustration of a flowchart of a process for controlling sensors in a sensor array is depicted in accordance with an illustrative embodiment. The process illustrated in this example may be used to select wavelengths that will be detected as part of wavelength windowing.

The process beings by selecting a group of wavelengths that are desired for detection by a sensor array (operation 700). The selection of the group of wavelengths may be based on wavelengths for potential inconsistencies that are not visible to a naked eye on the surface on the structure. In other words, the wavelengths are ones that are received when the potential inconsistencies are present on the surface on the structure. The process selectively activates a group of sensors to form a wavelength window that receives the group of wavelengths in a number of wavelengths (operation 702) with the process terminating thereafter.

Figure 8:
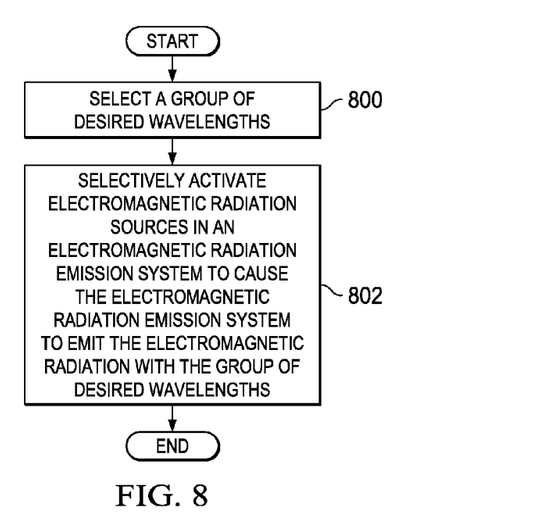
FIG. 8 is an illustration of a flowchart of a process for controlling electromagnetic radiation sources in an electromagnetic radiation emission system in accordance with an illustrative embodiment.

With reference now to FIG. 8, an illustration of a flowchart of a process for controlling electromagnetic radiation sources in an electromagnetic radiation emission system is depicted in accordance with an illustrative embodiment. The process illustrated in this example may be used to select wavelengths of electromagnetic radiation that will be transmitted towards a surface on a structure.

The process begins by selecting a group of desired wavelengths (operation 800). The group of desired wavelengths is selected based on wavelengths for potential inconsistencies that are not visible to a naked eye on the surface on the structure.

The process selectively activates electromagnetic radiation sources in an electromagnetic radiation emission system to cause the electromagnetic radiation emission system to emit the electromagnetic radiation with the group of desired wavelengths (operation 802). The process terminates thereafter.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent at least one of a module, a segment, a function, or a portion of an operation or step. For example, one or more of the blocks may be implemented as program code, hardware, or a combination of the program code and hardware. When implemented in hardware, the hardware may, for example, take the form of integrated circuits that are manufactured or configured to perform one or more operations in the flowcharts or block diagrams. When implemented as a combination of program code and hardware, the implementation may take the form of firmware. Each block in the flowcharts or the block diagrams may be implemented using special purpose hardware systems that perform the different operations or combinations of special purpose hardware and program code run by the special purpose hardware.

In some alternative implementations of an illustrative embodiment, the function or functions noted in the blocks may occur out of the order noted in the figures. For example, in some cases, two blocks shown in succession may be performed substantially concurrently, or the blocks may sometimes be performed in the reverse order, depending upon the functionality involved. Also, other blocks may be added in addition to the illustrated blocks in a flowchart or block diagram.

Figure 9:
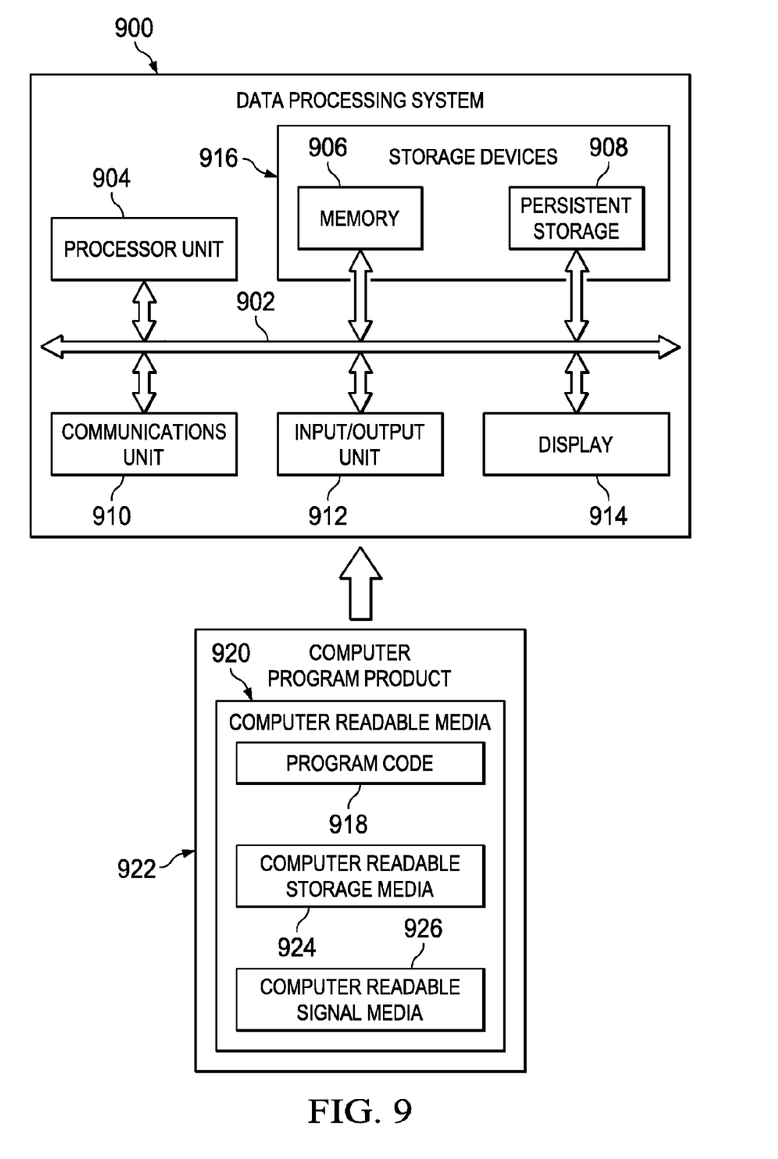
FIG. 9 is an illustration of a block diagram of a data processing system in accordance with an illustrative embodiment.

Turning now to FIG. 9, an illustration of a block diagram of a data processing system is depicted in accordance with an illustrative embodiment. Data processing system 900 may be used to implement computer system 256 in FIG. 2. In this illustrative example, data processing system 900 includes communications framework 902, which provides communications between processor unit 904, memory 906, persistent storage 908, communications unit 910, input/output (I/O) unit 912, and display 914. In this example, communications framework 902 may take the form of a bus system.

Processor unit 904 serves to execute instructions for software that may be loaded into memory 906. Processor unit 904 may be a number of processors, a multi-processor core, or some other type of processor, depending on the particular implementation.

Memory 906 and persistent storage 908 are examples of storage devices 916. A storage device is any piece of hardware that is capable of storing information, such as, for example, without limitation, at least one of data, program code in functional form, or other suitable information either on a temporary basis, a permanent basis, or both on a temporary basis and a permanent basis. Storage devices 916 may also be referred to as computer readable storage devices in these illustrative examples. Memory 906, in these examples, may be, for example, a random access memory or any other suitable volatile or non-volatile storage device. Persistent storage 908 may take various forms, depending on the particular implementation.

For example, persistent storage 908 may contain one or more components or devices. For example, persistent storage 908 may be a hard drive, a solid state hard drive, a flash memory, a rewritable optical disk, a rewritable magnetic tape, or some combination of the above. The media used by persistent storage 908 also may be removable. For example, a removable hard drive may be used for persistent storage 908.

Communications unit 910, in these illustrative examples, provides for communications with other data processing systems or devices. In these illustrative examples, communications unit 910 is a network interface card.

Input/output unit 912 allows for input and output of data with other devices that may be connected to data processing system 900. For example, input/output unit 912 may provide a connection for user input through at least one of a keyboard, a mouse, or some other suitable input device. Further, input/output unit 912 may send output to a printer. Display 914 provides a mechanism to display information to a user.

Instructions for at least one of the operating system, applications, or programs may be located in storage devices 916, which are in communication with processor unit 904 through communications framework 902. The processes of the different embodiments may be performed by processor unit 904 using computer-implemented instructions, which may be located in a memory, such as memory 906.

These instructions are referred to as program code, computer usable program code, or computer readable program code that may be read and executed by a processor in processor unit 904. The program code in the different embodiments may be embodied on different physical or computer readable storage media, such as memory 906 or persistent storage 908.

Program code 918 is located in a functional form on computer readable media 920 that is selectively removable and may be loaded onto or transferred to data processing system 900 for execution by processor unit 904. Program code 918 and computer readable media 920 form computer program product 922 in these illustrative examples. In one example, computer readable media 920 may be computer readable storage media 924 or computer readable signal media 926. In these illustrative examples, computer readable storage media 924 is a physical or tangible storage device used to store program code 918 rather than a medium that propagates or transmits program code 918.

Alternatively, program code 918 may be transferred to data processing system 900 using computer readable signal media 926. Computer readable signal media 926 may be, for example, a propagated data signal containing program code 918. For example, computer readable signal media 926 may be at least one of an electromagnetic signal, an optical signal, or any other suitable type of signal. These signals may be transmitted over at least one of communications links such as wireless communications links, optical fiber cable, coaxial cable, a wire, or any other suitable type of communications link.

The different components illustrated for data processing system 900 are not meant to provide architectural limitations to the manner in which different embodiments may be implemented. The different illustrative embodiments may be implemented in a data processing system including components in addition to or in place of those illustrated for data processing system 900. Other components shown in FIG. 9 can be varied from the illustrative examples shown. The different embodiments may be implemented using any hardware device or system capable of running program code 918.

Figure 10:
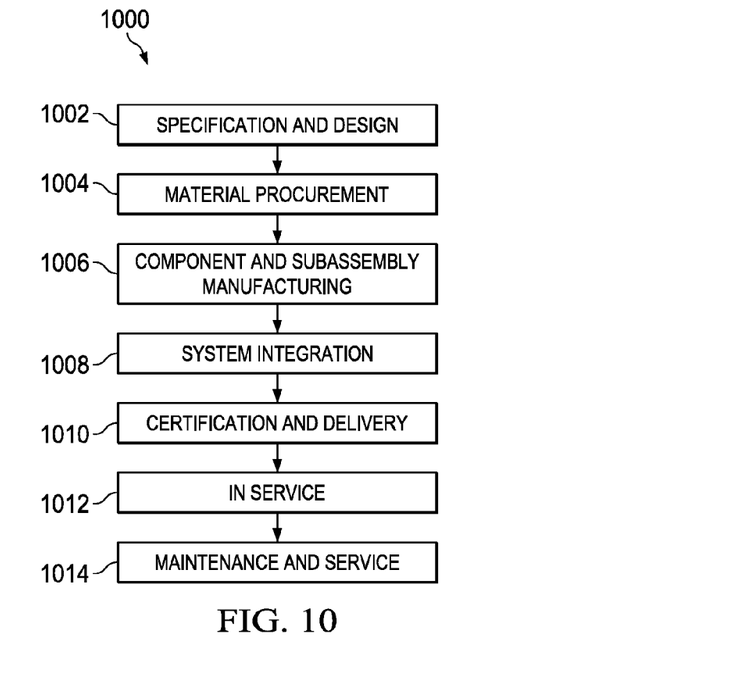
FIG. 10 is an illustration of a block diagram of an aircraft manufacturing and service method in accordance with an illustrative embodiment.
Figure 11:
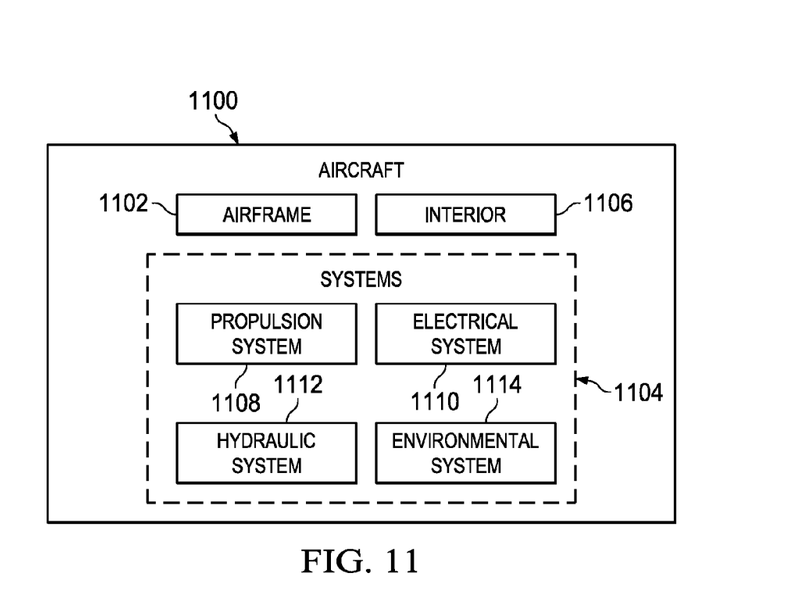
FIG. 11 is an illustration of a block diagram of an aircraft in which an illustrative embodiment may be implemented.

The illustrative embodiments of the present disclosure may be described in the context of aircraft manufacturing and service method 1000 as shown in FIG. 10 and aircraft 1100 as shown in FIG. 11. Turning first to FIG. 10, an illustration of a block diagram of an aircraft manufacturing and service method is depicted in accordance with an illustrative embodiment. During pre-production, aircraft manufacturing and service method 1000 may include specification and design 1002 of aircraft 1100 in FIG. 11 and material procurement 1004.

During production, component and subassembly manufacturing 1006 and system integration 1008 of aircraft 1100 takes place. Thereafter, aircraft 1100 may go through certification and delivery 1010 in order to be placed in service 1012. While in service 1012 by a customer, aircraft 1100 is scheduled for routine maintenance and service 1014, which may include modification, reconfiguration, refurbishment, and other maintenance or service.

Each of the processes of aircraft manufacturing and service method 1000 may be performed or carried out by a system integrator, a third party, an operator, or some combination thereof. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 11, an illustration of a block diagram of an aircraft is depicted in which an illustrative embodiment may be implemented. In this example, aircraft 1100 is produced by aircraft manufacturing and service method 1000 in FIG. 10 and may include airframe 1102 with plurality of systems 1104 and interior 1106. Examples of systems 1104 include one or more of propulsion system 1108, electrical system 1110, hydraulic system 1112, and environmental system 1114. Any number of other systems may be included. Although an aerospace example is shown, different illustrative embodiments may be applied to other industries, such as the automotive industry.

The apparatuses and methods embodied herein may be employed during at least one of the stages of aircraft manufacturing and service method 1000 in FIG. 10. In one illustrative example, components or subassemblies produced in component and subassembly manufacturing 1006 in FIG. 10 may be fabricated or manufactured in a manner similar to components or subassemblies produced while aircraft 1100 is in service 1012 in FIG. 10. As yet another example, one or more apparatus embodiments, method embodiments, or a combination thereof may be utilized during production stages, such as component and subassembly manufacturing 1006 and system integration 1008 in FIG. 10. For example, borescope system 204 in FIG. 2 may be used during any components or subassemblies produced in component and subassembly manufacturing 1006 when structures such as composite structures are laid up and cured.

One or more apparatus embodiments, method embodiments, or a combination thereof may be utilized while aircraft 1100 is in service 1012, during maintenance and service 1014 in FIG. 10, or both. For example, borescope system 204 in FIG. 2 may be used to perform inspections of aircraft during maintenance and service 1014 in FIG. 10 to determine whether inconsistencies are present that need maintenance.

The use of a number of the different illustrative embodiments may substantially expedite the assembly of aircraft 1100, reduce the cost of aircraft 1100, or both expedite the assembly of aircraft 1100 and reduce the cost of aircraft 1100. The use of borescope system 204 in FIG. 2 reduces the time needed to perform inspections of locations in structures that may be difficult to access with currently used inspection systems to perform a hyperspectral analysis to determine whether inconsistencies are present on the surfaces on the structures.

Thus, one or more of the illustrative examples provided have a technical solution that overcomes a technical problem with inspecting a composite structure that has limited access to locations. For example, in FIG. 2, borescope system 204 provides an ability to perform hyperspectral analysis 248 on surfaces 214 on structure 206 in a manner not currently available with current inspection systems. With this ability to perform hyperspectral analysis 248 at a variety of different locations, the time and effort needed to inspect structures to determine whether inconsistencies are present may be reduced.

The description of the different illustrative embodiments has been presented for purposes of illustration and description and is not intended to be exhaustive or limited to the embodiments in the form disclosed. The different illustrative examples describe components that perform actions or operations. In an illustrative embodiment, a component may be configured to perform the action or operation described. For example, the component may have a configuration or design for a structure that provides the component an ability to perform the action or operation that is described in the illustrative examples as being performed by the component.

Many modifications and variations will be apparent to those of ordinary skill in the art. Further, different illustrative embodiments may provide different features as compared to other desirable embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. An apparatus comprising
    a borescope inspection housing;
    an electromagnetic radiation emission system associated with the borescope inspection housing, wherein the electromagnetic radiation emission system is configured to emit electromagnetic radiation;
    a filter located inside of the borescope inspection housing, wherein the filter is configured to pass a number of wavelengths in a response to the electromagnetic radiation directed at a surface on a structure, wherein the response is received through an opening in the borescope inspection housing; and
    a sensor array located behind the filter inside of the borescope inspection housing, wherein the sensor array comprises sensors configured to generate data from the number of wavelengths passed by the filter, enabling a hyperspectral analysis of the surface on the structure.

2. The apparatus of claim 1 further comprising:
    an analyzer in communication with the sensor array, wherein the analyzer selectively activates a group of sensors in the sensor array to form a wavelength window that receives a group of wavelengths in the number of wavelengths.

3. The apparatus of claim 2, wherein the group of wavelengths is selected based on the wavelengths for a group of inconsistencies not visible to a naked eye on the surface on the structure.

4. The apparatus of claim 1 further comprising:
    an analyzer in communication with the electromagnetic radiation emission system, wherein the analyzer selectively activates electromagnetic radiation sources in the electromagnetic radiation emission system to cause the electromagnetic radiation emission system to emit the electromagnetic radiation with a group of desired wavelengths.

5. The apparatus of claim 4, wherein the group of desired wavelengths is selected based on wavelengths for a group of inconsistencies not visible to a naked eye on the surface on the structure.

6. The apparatus of claim 1, wherein the response is from a location on the surface and further comprising:
    an analyzer in communication with the sensor array and configured to cause the sensor array to generate the data from the response received from the electromagnetic radiation directed to the surface on the structure and generate a two-dimensional image of the surface on the structure with a group of graphical indicators indicating a group of inconsistencies not visible to a naked eye in the location.

7. The apparatus of claim 6, wherein the analyzer communicates with the sensor array using at least one of an electrical wire, an optical fiber, or a wireless connection.

8. The apparatus of claim 1 further comprising:
    an elongate member associated with the borescope inspection housing to form a borescope system, wherein the elongate member is selected from one of a rigid elongate member, a flexible elongate member, a cable, a tube, and a pipe.

9. The apparatus of claim 1, wherein the filter is an interference filter.

10. The apparatus of claim 1 further comprising:
    a lens that seals the opening in the borescope inspection housing, wherein the response passes through the lens to reach the filter.

11. The apparatus of claim 1, wherein the sensors are selected from a group of sensors selected from at least one of a charged coupled device, a complementary metal oxide semiconductor device, an indium antimonide (InSb) semiconductor device, or a mercury cadmium telluride (HgCdTe) semiconductor device.

12. The apparatus of claim 1, wherein the electromagnetic radiation emission system comprises a group of electromagnetic radiation sources selected from at least one of a light emitting diode, a halogen light bulb, or an incandescent light bulb.

13. The apparatus of claim 1, wherein the structure is selected from one of an uncured composite structure, a cured composite structure, a part, an assembly, a wing, a composite skin panel, a horizontal stabilizer, a spar, a rib, layers of prepreg, an engine housing, a wing box, a pipe, and a tube.

14. A hyperspectral borescope system comprising:
    a borescope inspection housing for a borescope;
    a tube associated with the borescope inspection housing for the borescope;

an electromagnetic radiation emission system associated with the borescope inspection housing, wherein the electromagnetic radiation emission system is configured to emit electromagnetic radiation;

a filter located inside of the borescope inspection housing, wherein the filter is configured to pass a number of wavelengths in a response to the electromagnetic radiation directed at a surface on a structure, wherein the response is received through an opening in the borescope inspection housing;

a sensor array located behind the filter inside of the borescope inspection housing, wherein the sensor array comprises sensors configured to generate data from the number of wavelengths passed by the filter; and an analyzer in communication with the sensor array and configured to cause the sensor array to generate the data from the response received from the electromagnetic radiation directed to the surface on the structure and generate a two-dimensional image of the surface on the structure with a group of graphical indicators indicating a group of inconsistencies not visible to a naked eye.

15. The hyperspectral borescope system of claim 14, wherein the analyzer is configured to selectively activate a group of sensors to form a wavelength window that receives a group of wavelengths in the number of wavelengths, wherein the group of wavelengths is selected based on wavelengths for the group of inconsistencies not visible to the naked eye on the surface on the structure.

16. The hyperspectral borescope system of claim 14, wherein the analyzer is configured to selectively activate electromagnetic radiation sources to cause the electromagnetic radiation emission system to emit the electromagnetic radiation with a group of desired wavelengths, wherein the group of desired wavelengths is selected based on wavelengths for the group of inconsistencies not visible to the naked eye on the surface on the structure.

17. A method for inspecting a structure, the method comprising:

sending electromagnetic radiation to a surface on the structure from an electromagnetic radiation emission system;

filtering a response to the electromagnetic radiation using a filter located inside of a borescope inspection housing, wherein the filter is configured to pass a number of wavelengths in a response to the electromagnetic radiation directed at the surface on the structure;

generating data from the number of wavelengths from the number of wavelengths passed through the filter using a sensor array; and generating a two-dimensional image of the surface on the structure with a group of graphical indicators indicating a group of inconsistencies not visible to a naked eye, wherein the two-dimensional image is generated using data from the sensor array.

18. The method of claim 17 further comprising:

selectively activating a group of sensors to form a wavelength window that receives a group of wavelengths in the number of wavelengths, wherein the group of wavelengths is selected based on wavelengths for the group of inconsistencies not visible to the naked eye on the surface on the structure.

19. The method of claim 17 further comprising:

selectively activating electromagnetic radiation sources in the electromagnetic radiation emission system to cause the electromagnetic radiation emission system to emit the electromagnetic radiation with a group of desired wavelengths, wherein the group of desired wavelengths is selected based on wavelengths for the group of inconsistencies not visible to the naked eye on the surface on the structure.

20. The method of claim 17, wherein the filter is an interference filter.

21. The method of claim 17, wherein the structure is selected from one of an uncured composite structure, a cured composite structure, a part, an assembly, a wing, a composite skin panel, a horizontal stabilizer, a spar, a rib, layers of prepreg, an engine housing, a wing box, a pipe, and a tube.

* * * * *

UNITED STATES PATENT AND TRADEMARK OFFICE
CERTIFICATE OF CORRECTION

PATENT NO.         : 9,955,088 B2
APPLICATION NO.    : 15/178617
DATED              : April 24, 2018
INVENTOR(S)        : Motzer et al.

Page 1 of 1

It is certified that error appears in the above-identified patent and that said Letters Patent is hereby corrected as shown below:

In the Claims

Column 16, Line 8, change "on the wavelengths" to read --on wavelengths--
Column 18, Line 7, change "in a response" to read --in the response--
Column 18, Line 15, change "data" to read --the data--

Signed and Sealed this
Twenty-third Day of October, 2018

Andrei Iancu
*Director of the United States Patent and Trademark Office*